(12) United States Patent
Bichler et al.

(10) Patent No.: US 10,687,946 B2
(45) Date of Patent: Jun. 23, 2020

(54) DEVICE FOR STABILISING JOINTS

(71) Applicant: BETTERGUARDS TECHNOLOGY GmbH, Berlin (DE)

(72) Inventors: Vinzenz Bichler, Berlin (DE); Timo Stumper, Berlin (DE); Oscar Buschinger, Berlin (DE)

(73) Assignee: Betterguards Technology GmbH, Berlin (DE)

( * ) Notice: Subject to any disclaimer, the term of this patent is extended or adjusted under 35 U.S.C. 154(b) by 0 days.

(21) Appl. No.: 15/441,947

(22) Filed: Feb. 24, 2017

(65) Prior Publication Data
US 2017/0304057 A1    Oct. 26, 2017

(30) Foreign Application Priority Data
Apr. 25, 2016   (DE) .......................... 10 2016 107 664

(51) Int. Cl.
*F16F 9/19*     (2006.01)
*A61F 2/30*     (2006.01)
(Continued)

(52) U.S. Cl.
CPC .............. *A61F 2/30* (2013.01); *A61F 5/0104* (2013.01); *A61F 5/0111* (2013.01); *F16F 9/19* (2013.01);
(Continued)

(58) Field of Classification Search
CPC .......... F16F 9/3405; F16F 9/19; F16F 9/5126; F16F 9/53; F16F 2222/12;
(Continued)

(56) References Cited

U.S. PATENT DOCUMENTS

| | | | |
|---|---|---|---|
| 4,541,289 A | * | 9/1985 | Valdemarsson ......... G01L 1/127 73/862.69 |
| 4,654,396 A | | 3/1987 | Bung et al. |

(Continued)

FOREIGN PATENT DOCUMENTS

| | | |
|---|---|---|
| CA | 1 163 033 | 2/1984 |
| DE | 30 25 562 A1 | 2/1982 |

(Continued)

OTHER PUBLICATIONS

European Search Report for the Corresponding Application EP17157941, dated Sep. 25, 2017, 7 pages.

*Primary Examiner* — Melody M Burch
(74) *Attorney, Agent, or Firm* — Ohlandt, Greeley, Ruggiero & Perle, L.L.P.

(57) ABSTRACT

The present invention relates to a device (1) for stabilising joints, comprising a receptacle (20), wherein the receptacle (20) is filled with a filling medium (30), a first body (40) for interaction with the filling medium (30), wherein the first body is arranged displaceably in the receptacle (20), a force-transmission means (50) for the transmission of an external force onto the first body (40), a second body (60) for interaction with the filling medium (30) which is arranged displaceably in the receptacle (20), wherein the second body is coupled elastically to the first body (40) via a coupling element (70), wherein at least one of the second body (60) and the first body (40) have at least one outlet opening (64) through which the filling medium (30) can flow, and wherein the first body (40) forms a valve body and the second body (60) forms a valve seat so that a flow of the filling medium (30) through the outlet opening (64) can be allowed or prevented as a function of the valve position.

13 Claims, 3 Drawing Sheets

(51) Int. Cl.
*F16F 9/516* (2006.01)
*A61F 5/01* (2006.01)
*F16F 9/512* (2006.01)
*F16F 9/34* (2006.01)
*F16F 9/53* (2006.01)
*A61F 2/50* (2006.01)
*F16F 9/30* (2006.01)
*F16F 9/32* (2006.01)

(52) U.S. Cl.
CPC ............ *F16F 9/3405* (2013.01); *F16F 9/512* (2013.01); *F16F 9/516* (2013.01); *F16F 9/5126* (2013.01); *F16F 9/53* (2013.01); *A61F 2002/30558* (2013.01); *A61F 2002/30579* (2013.01); *A61F 2002/30601* (2013.01); *A61F 2002/5001* (2013.01); *A61F 2005/0165* (2013.01); *A61F 2005/0169* (2013.01); *A61F 2250/0073* (2013.01); *F16F 9/30* (2013.01); *F16F 9/3214* (2013.01); *F16F 2222/02* (2013.01); *F16F 2222/12* (2013.01); *F16F 2224/041* (2013.01); *F16F 2228/066* (2013.01)

(58) Field of Classification Search
CPC ...... F16F 2228/066; F16F 9/516; F16F 9/512; F16F 9/30; F16F 9/3214; F16F 2224/041; F16F 2222/02; A61F 2/30; A61F 2002/30601; A61F 2002/30579; A61F 2002/30558; A61F 2005/0169; A61F 2005/0165; A61F 2250/0073; A61F 5/0104; A61F 5/0111; A61F 2002/5001
See application file for complete search history.

(56) References Cited

U.S. PATENT DOCUMENTS

| | | | |
|---|---|---|---|
| 4,973,077 A * | 11/1990 | Kuwayama | B60G 21/0553 188/318 |
| 5,037,880 A | 8/1991 | Schmidt et al. | |
| 5,190,126 A * | 3/1993 | Curnutt | F16F 9/06 188/269 |
| 6,129,343 A * | 10/2000 | Ecarnot | F16F 9/0209 188/281 |
| 2008/0296526 A1* | 12/2008 | Baalmann | F16F 9/3485 251/337 |
| 2014/0015176 A1 | 1/2014 | Wetzel et al. | |
| 2016/0331569 A1 | 11/2016 | Bichler et al. | |
| 2017/0151082 A1 | 6/2017 | Bichler | |

FOREIGN PATENT DOCUMENTS

| | | |
|---|---|---|
| DE | 34 33 085 A1 | 3/1986 |
| DE | 39 17 456 A1 | 12/1990 |
| DE | 10 2014 107 335 A1 | 1/2016 |
| EP | 1 443 097 A1 | 8/2004 |
| EP | 2842527 A1 | 3/2015 |
| EP | 3092980 A1 | 11/2016 |
| WO | 2013/174989 A1 | 11/2013 |
| WO | 2015177357 A1 | 11/2015 |

\* cited by examiner

DEVICE FOR STABILISING JOINTS

CROSS REFERENCE TO RELATED APPLICATION

The present application claims foreign priority to German Patent Application No. DE 10 2016 107 664.3 filed on Apr. 25, 2016, the entirety of which is incorporated by reference hereby.

TECHNICAL FIELD

The present invention relates to a device for stabilising joints, which comprises a receptacle, wherein the receptacle is filled with a filling medium, a first body for interaction with the filling medium, wherein the first body is arranged displaceably in the receptacle, and a means for the transmission of an external force onto the first body.

PRIOR ART

It is known to stabilise joints, muscles and tendons by means of devices which enable an adaptive restriction of movement. Among other things, the adaptive behaviour of such devices is achieved in that two bodies move relative to one another, wherein a shear-thickening fluid is located between the bodies. The opposing surfaces of the bodies form shear surfaces which, as a result of the relative movement, introduce shear forces into the shear-thickening fluid. The greater the shear forces, the more viscous the shear-thickening fluid behaves. From a defined shear speed, the shear-thickening fluid experiences a shear jump, as a result of which the degree of viscosity rapidly increases.

The devices are fixed between two body points of a user. Here, a shear body of the device forms a receptacle which is filled with the shear-thickening fluid. The other shear body forms an extraction body which is arranged movably in the receptacle. If physiological forces, i.e. non-critical forces for the body part to be correspondingly stabilised, are introduced via the two body points of the user into the device, as a result of the fluid state of the shear-thickening fluid, a relative movement of the receptacle and the extraction body and thus a movement of the body part to be stabilised are permitted.

However, if non-physiological forces, i.e. forces which are critical for the body part to be correspondingly stabilised, are introduced into the device, the shear forces proceeding from the shear surfaces of the receptacle and the extraction body bring about a shear hardening of the shear-thickening fluid, as a result of which a relative movement between the extraction body and the receptacle is now only possible with a very high force outlay.

Such a device is known, for example, from WO 2013/174989 A1 which shows an orthopaedic device for restricting the movement of a joint arranged between a first and a second body region.

In the case of the known devices, however, the maintenance of the shear hardening is only carried out over a relatively short period of time. Shortly after the impulse which triggers the shear hardening abates, i.e. as soon as the speed of the action of force is reduced, the stabilising retention force provided by the device also falls away again.

This is problematic precisely when, after an abrupt, non-physiological action of force on the body part to be protected, a force remains which acts significantly more slowly on the body part. After the protecting action of the device falls away, the body part is exposed to this force in an unhindered manner.

This can occur, for example, in the region of the ankle joint. Here, the forces which occur with a high speed can initially be compensated for by the device during bending over. However, if the action of the device is reduced, smaller, slower movements which are brought about, for example, as a result of body weight cannot be prevented since the shear-thickening medium is not hardened in the case of these low speeds. This can result in continuation of the bending over movement.

Explanation of the Invention

Proceeding from the known prior art, one object is to indicate an improved device for stabilisation of joints, in particular the protective action of the device should last as long as possible.

This object is achieved by means of a device with the features of Claim 1. Further embodiments will become apparent from the subordinate claims.

A device for stabilising joints is correspondingly indicated, which comprises a receptacle, wherein the receptacle is filled with a filling medium, a first body for interaction with the filling medium, wherein the first body is arranged displaceably in the receptacle, and a force-transmission means for transmission of an external force onto the first body. A second body for interaction with the filling medium is arranged displaceably in the receptacle, wherein the second body is coupled elastically to the first body via a coupling element. At least one of the second body and the first body have at least one outlet opening through which the filling medium can flow. The outlet opening in the second body and/or the first body represents an additional flow path for the filling medium through which the filling medium can flow as long as there is a distance between the first body and the second body.

Furthermore, the first body forms a valve body and the second body forms a valve seat so that a flow of the medium through the outlet opening can be allowed or prevented as a function of the valve position. In the closed valve position, the filling medium can still only flow in the region between the receptacle and the shear surfaces of the first body and the second body in so far as the degree of increase in shear stress allows this.

As a result, it is possible to transmit external forces acting on the first body via the coupling element to the second body. The first body is correspondingly able to push and/or pull the second body by means of the coupling element through the filling medium.

Here, the shear surfaces of the first body and the second body are configured in such a manner that, when an external force acts on the first body with a speed in the physiological range, both bodies can be moved through the filling medium. The coupling element is additionally configured in such a manner that, when an external force acts on the first body, in the range of a physiological speed, it transmits a force onto the second body so that it can be moved together with the first body through the filling medium.

If the force acting via the first body and the coupling element on the second body reaches a critical speed, i.e. a non-physiological speed, an increase in shear stress occurs at the shear surfaces of the second body. As a result of this increase in shear stress, the filling medium exerts a resistance force counter to the movement of the second body.

If this resistance force reaches a value of greater than or equal to the force acting from the coupling element on the second body, the second body cannot be moved further through the filling medium and is blocked by it.

An increase in shear stress also occurs in the region of the shear surfaces of the first body as soon as the speed at which the first body is moved by means of the external force through the filling medium reaches a critical value, i.e. a non-physiological speed. A resistance force then proceeds from the filling medium, which resistance force acts counter to the external force acting on the first body. In this case, the first body can be moved through the filling medium until the resistance force proceeding from the filling medium is equal to the external force acting on the first body.

In the event that the second body is blocked by the resistance force proceeding from the filling medium, while the external force acting on the first body is greater than the resistance force proceeding from the filling medium, the first body can be moved relative to the second body. If the external force acts on the first body in such a manner that the distance between the first body and the second body is reduced, the distance between the first body and the second body can be closed. In this state, both the resistance force generated on the shear surfaces of the first body and the resistance force generated on the shear surfaces of the second body act counter to the external force bearing against the first body. As a result of the overall larger shear surface, the increase in shear stress can arise more rapidly and intensively so that the device reacts in general more rapidly and with higher retention forces. This is above all advantageous against the background of providing a protective effect after a period of time which is shorter than the reaction time of the muscles of the user.

Movements of joints can be easily braked as a result. The increase in shear stress of the filling medium in the region of the overall larger shear surface can furthermore be maintained for longer as a result. In order to move the first body and the second body in the state lying against one another, a significantly larger external force is required than in the case of the movement of the first body and the second body in the state spaced apart from one another. The increase in shear stress in the state lying against one another can thus also be maintained in the case of significantly more slowly acting forces.

This is useful, for example, for applications of the devices in the region of the ankle since, after bending over, the entire body weight usually loads the ankle. The force acting on the joint as a result of the bending over movement and the subsequent force acting more slowly on the joint as a result of body weight can be correspondingly counteracted by means of the device. The device can correspondingly also provide a holding force if the primary impulse, i.e. the acting force, decreases with high speed.

In another embodiment, the shear surface of the first body and the shear surface of the second body have a different size. The surfaces with respect to which the filling medium carries out a relative flow movement when the first body and/or the second body are moved as a result of an external force are defined as shear surfaces of the first body and of the second body. When a critical shear speed is reached which is due to the external force acting on the first body, an increase in shear stress occurs in the filling medium in the surroundings of the shear surfaces.

As a result of the selection of shear surfaces of different sizes in terms of the first body in relation to the second body, it is possible to specify the interaction of the first body and of the second body with the filling medium and thus the resistance force acting in each case on the bodies, in the case of a given bearing external force. As a result, a different behaviour of the first body and of the second body can be achieved in the case of an external force acting on the first body.

In another embodiment, the shear surface of the first body is smaller than the shear surface of the second body. As a result, it is possible that, if the first body and the second body are moved through the filling medium as a result of an external force applied to the first body, a greater resistance force acts on the second body than on the first body. The second body correspondingly has a critical shear speed which is lower than the critical shear speed of the first body. If the bodies reach the critical shear speed of the second body as a result of the application of the external force, the second body is blocked as a result of the increase in shear stress of the filling medium in the region of the shear surfaces of the second body, while the first body can still be moved through the shear-thickening medium. In other words, when the critical shear speed of the second body is reached, the resistance force acting on the second body is equal to the force proceeding from the elastic coupling element, while the resistance force acting on the first body is still smaller than the external force acting on the first body.

As a result, the first body is moved towards the second body until the distance between the first body and the second body is closed. In the closed state, the resistance force which is produced from the interaction of the sum of the shear surfaces of the first body and the second body with the filling medium counteracts the external force. The increase in shear stress thus already occurs at lower speeds or the increase in shear stress is maintained in the case of further acting forces with low speeds so that the device reacts overall more rapidly and with a higher retaining force.

In one further development, a gap dimension between the first body and the receptacle is different from a gap dimension between the second body and the receptacle. The gap dimension represents the smallest cross-sectional surface through which the filling medium can flow relative to the first body or the second body. The cross-sectional surface lies in a plane perpendicular to a main direction of movement of the first body and of the second body.

The critical shear speed of the first body and of the second body can be influenced via the gap dimension. By virtue of the fact that the first body and the second body are at different distances from the lateral wall of the receptacle, it is possible that the filling medium can flow with different speeds past the first body and the second body.

As a result, it can be achieved that the critical shear speed of the first body differs from the critical shear speed of the second body.

In a further embodiment, the gap dimension between the first body and the receptacle is larger than the gap dimension between the second body and the receptacle. This can be achieved, for example, by a conically tapering receptacle. As a result, it is possible that, if the first body and the second body are moved through the filling medium as a result of an external force applied onto the first body, a greater resistance force acts on the second body than on the first body. The second body correspondingly has a critical shear speed which is lower than the critical shear speed of the first body. If the bodies reach the critical shear speed of the second body by applying the external force, the second body is blocked as a result of the increase in shear stress of the filling medium in the region of the shear surfaces of the second body, while the first body can still move through the filling medium. In other words, when the critical shear speed of the second body is reached, the resistance force acting on the second body is equal to the force proceeding from the elastic coupling element, while the resistance force acting on the first body is still smaller than the external force acting on the first body.

In a further embodiment, the coupling element comprises at least one spring element. Here, the spring element can comprise a pressure spring, a tension spring and/or an elastic polymer. The start of a jump in dilatancy of the device for example can be defined on the basis of the spring force of the spring element. The second body is correspondingly blocked in its movement if the resistance force, which is a result of the increase in shear stress of the filling medium and acts on the second body, is equal to the spring force of the spring element.

Once the second body is blocked as a result of the increase in shear stress of the filling medium, the spring element is compressed by the continuing movement of the first body towards the second body.

In a further configuration, the coupling element is manufactured from a material with a temperature-dependent modulus of elasticity. As a result, temperature fluctuations which have an effect on the behaviour of the filling medium can be compensated for. Fluctuations in the temperature of the device can be caused, for example, by the body temperature of the user or the ambient temperature. Since the viscosity of the filling medium reduces with rising temperature, irregularities in the onset of the jump in dilatancy can arise. This means that, at higher temperatures, the jump in dilatancy begins later than in the case of low temperatures.

The temperature-induced fluctuations in the onset of the jump in dilatancy can be counteracted by the use of a coupling element with a temperature-dependent modulus of elasticity. In this case, the temperature dependency of the coupling element can be defined in such a manner that the modulus of elasticity of the coupling element reduces with rising temperature. This has the result that, if the necessary critical shear speed increases with rising temperature, at which speed the second body moves through the filling medium in order to be braked by it, the force proceeding from the elastic coupling element is simultaneously reduced. The resistance force acting on the second body which is required in order to block the second body correspondingly falls with increasing temperature. For example, the coupling element can be designed in the form of a spring element, wherein the spring constant varies as a function of the temperature, as a result of which an alignment of the varying viscosity of the filling medium can be carried out.

It is thus overall possible to compensate for the temperature fluctuations acting on the device so that the first body behaves almost homogeneously even in the case of different prevailing temperatures when the external force acts indirectly on the second body.

In another configuration, the outlet opening can be closed by means of the first body and/or the second body so that a flow of the medium through the outlet opening can be prevented. If the first body is moved by the external force so far towards the second body that the distance between the bodies is closed, the outlet opening is also closed so that the filling medium can still only flow between the outer surfaces of the first body and of the second body and the inner surface of the receptacle in so far as a degree of shear hardening allows this. The same also applies in reverse in the event that the first body has at least one outlet opening.

In one further development, the force-transmission means for transmission of the external force is formed in one piece with the first body. In this case, the first body forms jointly with the force-transmission means an extraction body, wherein that end of the force-transmission means lying outside the device is connected to a body part of the user and the receptacle is connected to a different body part of the user.

In a further embodiment, the first body can exert a compressive force and/or a tractive force on the second body by means of the coupling element. If the first body is moved away from the second body by the action of an external force, the second body can be pulled along via the elastic coupling element by the first body. If, however, the first body is moved by the external force in the direction of the second body, the first body can push the second body in the same direction of movement via the elastic coupling element.

In a further embodiment, the size of the shear surface of the first body, and the size of the shear surface of the second body are configured in such a manner that, if the external force acts with a speed below a threshold value on the first body, the first body and the second body can be moved almost uniformly through the filling medium, and that, if the external force acts with a speed greater than or equal to the threshold value on the first body, the first body and the second body can be moved relative to one another. In this case, the threshold value of the speed represents the value at which the resistance force as a result of the shear stress is just as large as the resistance force of the elastic coupling element.

In one further development, the filling medium is a fluid. For example, Newtonian fluids such as, for example, silicon oil can be used as the filling medium. Newtonian fluids exhibit a linear behaviour, i.e. the shear stress increases linearly with the shear speed. Speed-dependent damping is possible as a result of this.

In a further development, the filling medium is shear-thickening. For example, the filling medium can be a shear-thickening fluid. The term shear-thickening fluids generally and in particular in the present invention is to be understood as copolymer dispersions such as are shown, for example, in DE 30 25 562 A1, DE 34 33 085 A1 and DE 39 17 456 A1. The dispersions are composed, for example, of emulsion copolymerisates and metal salts. The emulsion copolymerisates can be polymerised, for example, from 1-10% by weight monoolefinically unsaturated mono- and/or dicarboxylic acids, such as acrylic, methacrylic, maleic and/or fumaric acid, 99-90% by weight other olefinically unsaturated monomers, such as styrol, C1-C6-alkylacrylates, such as methyl methacrylate, and 5-30% by weight of a carboxylic acid alyl ester monomer with two or more copolymerisable double bonds such as, for example, diallyl phthalate.

In general 0.1 to 30% by weight in relation to the copolymerisates of metal oxides, hydroxides, halogenides, carbonates, hydrogen sulphates, sulphates and/or phosphates are added as metal salts. The shear-thickening fluids furthermore contain diluting agents such as alcohols, glycols, di- and triglycols, formamides and/or water. For a detailed composition of the shear-thickening fluid, reference is made to DE 30 25 562 A1, DE 39 17 456 A1 and to EP 1 443 097 A1. Moreover, shear-thickening fluids can also be simple dispersions which have shear-thickening properties from a certain solid content.

BRIEF DESCRIPTION OF THE FIGURES

Further embodiments and aspects of the present invention will be explained in greater detail by the following description of the figures. In the figures.

DETAILED DESCRIPTION OF EXEMPLARY EMBODIMENTS

Figure 1C:
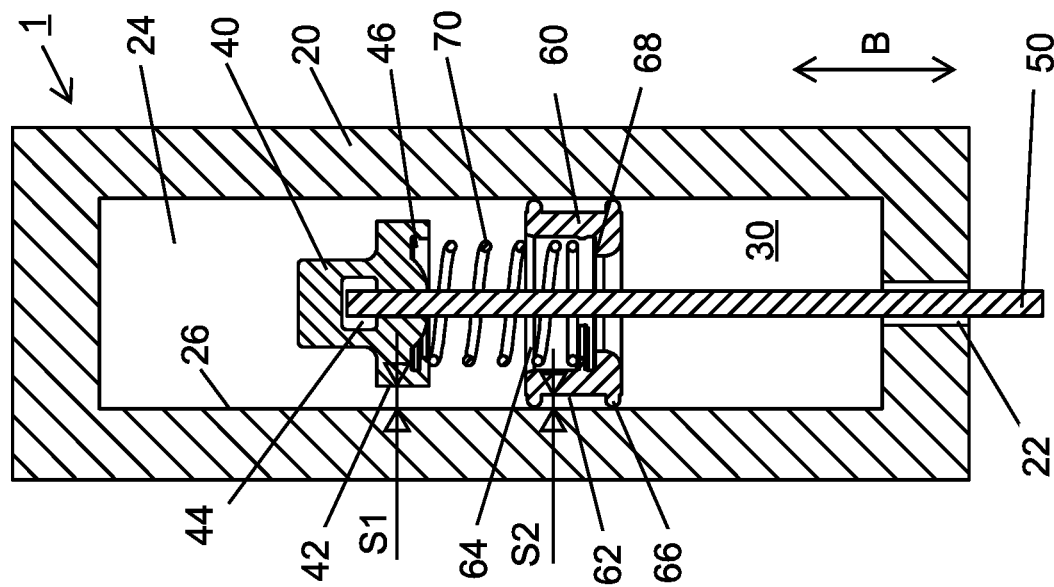
FIG. 1C shows a sectional view of the device from FIG. 1A in an initial state.
Figure 1B:
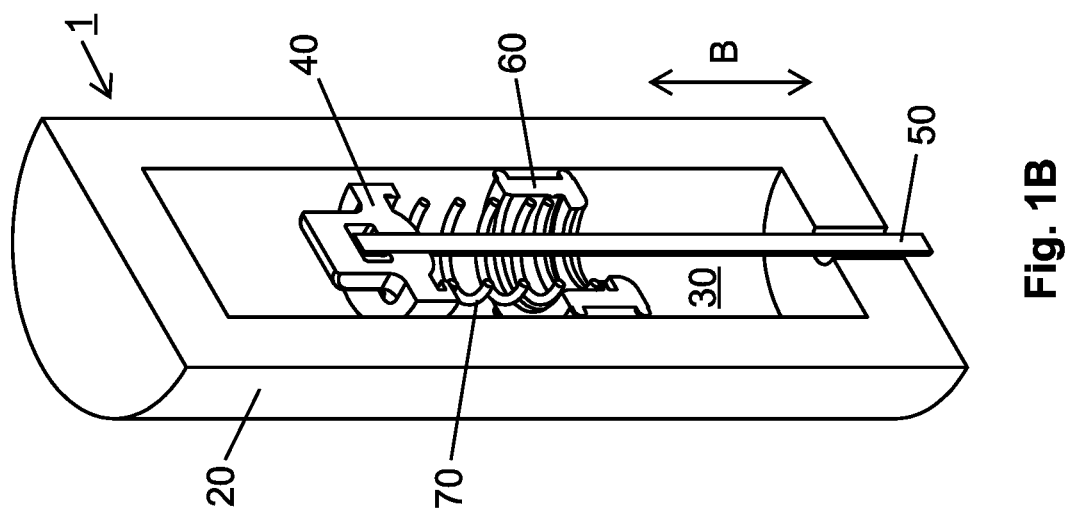
FIG. 1B shows a perspective sectional view of the device from FIG. 1A in an initial state.
Figure 1A:
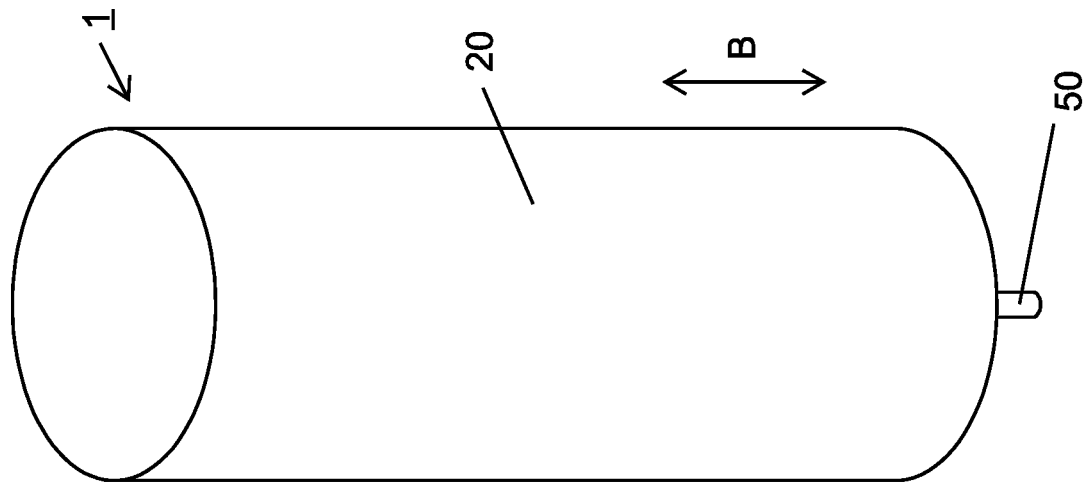
FIG. 1A shows a perspective view of a device for stabilising joints.

A perspective view of a device 1 for stabilising joints can be inferred from FIG. 1A. A force-transmission means 50 protrudes out of a cylindrical receptacle 20. In this case, the receptacle can be fastened to a body part of a user and force-transmission means 50 to a different body part of the user. Direction B represents the direction of movement of the device. Alternatively, the receptacle can also be formed to be quadratic.

The interior of device 1, which is in an initial state, can be inferred from FIGS. 1B and 1C. Device 1 comprises a receptacle 20 which can be fastened to a region of the body of a user. Receptacle 20 20 has an opening 22 through which a force-transmission means 50 projects into the inner space of device 20. The end of force-transmission means 50, which lies outside device 20, can be fastened to a different region of the body of the user.

If the body region of the user to which receptacle 20 is fastened moves relative to the body region of the user on which force-transmission means 50 is arranged, force-transmission means 50 moves relative to receptacle 20. In particular, force-transmission means 50 can move in a main direction of movement B further into receptacle 20 or further out of receptacle 20. The receptacle of the device is manufactured from plastic. Among other things, fibre-reinforced plastics can also be used. Alternatively, the receptacle can also be manufactured from metals such as, for example, aluminium or magnesium. Moreover, the receptacle can also be manufactured from ceramic. Force-transmission means 50 is a rod element made of plastic. Alternatively, the force-transmission means can also be formed to be fibrous. Moreover, the force-transmission means can also be manufactured from metal such as, for example, aluminium, magnesium or steel.

The inner space of device 20 is filled with a filling medium 30. Filling medium 30 is a dilatant fluid. Alternatively, Newtonian fluids such as, for example, silicon oil can be used as filling medium. Moreover, a shear-thickening plastic can also be used. The plastic is present in this case in powder form. Moreover, sand can also be used as the medium.

Furthermore, a first body 40 is arranged in inner space 24 of device 20 and is movable in direction of movement B relative to receptacle 20 through filling medium 30. First body 40 is coupled at a force-transmission region 44 to the force-transmission means 50 so that a force proceeding from force-transmission means 50 can be transmitted to first body 40.

The surface of first body 40, relative to which the filling medium flows if first body 40 is moved in direction of movement B, forms a shear surface 42. An increase in shear stress arises in the region of shear surface 42 as a result of the filling medium if first body 40 is moved with a non-physiological speed through the filling medium.

A gap dimension S1 represents the minimal distance between shear surface 42 of first body 40 and inner surface 26 of the receptacle. First body 40 is manufactured from plastic. Alternatively, the first body can also be manufactured from a metal such as, for example, aluminium.

A second body 60 which is movable relative to receptacle 20 in direction of movement B is furthermore arranged in inner space 24 of receptacle 20. The outer circumferential surface of second body 60 forms a shear surface 62. Second body 60 comprises guide projections 66 which can contact the inner space of receptacle 20 in a punctiform manner in order to movably guide second body 60 in inner space 24 of receptacle 20.

The smallest distance between shear surface 62 and inner surface 26 of receptacle 20 forms gap dimension S2. Second body 60 is manufactured from plastic. Alternatively, the second body can also be manufactured from a metal such as, for example, aluminium.

First body 40 is coupled to second body 60 via an elastic coupling element 70. Elastic coupling element 70 shown in FIGS. 1B and 1C is formed by a spring which is mounted at one end in a spring seat 46 of first body 40 and at the other end in a spring seat 68 of second body 60. According to the direction of movement B in which a force acts on force-transmission means 50, second body 60 can be pulled or pushed via coupling element 70 by means of first body 40. In this case, the spring can be manufactured from plastic or from metal. Alternatively, elastic coupling element 70 can also be formed in the form of an elastic polymer or rubber.

In one further alternative, the first body, the second body and the elastic coupling element are injection moulded in one piece.

Second body 60 furthermore comprises an outlet opening 64 through which filling medium 30 can flow. If second body 60 is correspondingly moved by a force proceeding from coupling element 70 relative to receptacle 20, shear-thickening medium 30 can flow both externally in the region of gag dimension S2 and internally through outlet opening 64 along the second body.

Device 1 shown in FIGS. 1A to 1C is designed for tensile loads. I.e. also loads which result from a moving away from one another of the body region of the user to which receptacle 20 is fastened and of the body region of the user to which force-transmission means 50 is fastened. If force-transmission means 50 is pulled out of device 20, it pulls second body 40 with it, as a result of which the latter pushes onto second body 60 by means of coupling element 70. Force-transmission means 50 is embodied to be rod-shaped and extends from first body 40 through outlet opening 64 of second body 60 and finally through opening 22 of receptacle 20. Sealing means, which are not represented in FIGS. 1A and 1B and seal off inner space 24 of receptacle 20 from the surroundings, are arranged in the region of opening 22 so that filling medium 30 can be kept in inner space 24 of receptacle 20.

The function of the device is described below on the basis of FIGS. 1B to 2B. If a force acts in the range of a physiological speed on force-transmission means 50 so that first body 40 is pulled in the direction of opening 22, second body 60 is also pushed by means of coupling element 70 in the direction of opening 22. Depending on the size of shear surface 62 and/or gap dimension S2, a threshold valve can be defined which specifies a speed of the second body in the case of which an increase in shear stress arises as a result of the flow of filling medium 30 along shear surface 62 which does not allow any further movement of second body 60. This threshold value can furthermore be influenced by the properties of elastic coupling element 70. In the case of coupling element 70 shown in FIGS. 1A and 1B in the form of a spring, a standstill of second body 60 comes about if the resultant holding force generated in the region of shear surface 62 is greater than or equal to a spring force proceeding from the spring.

Once second body 60 has been blocked as a result of the shear hardening in the region of shear surface 62, the force acting on force-transmission means 50 moves second body 40 furthermore in the direction of opening 22. In this case, filling medium 30 can flow along shear surface 42 of first body 40 and through outlet opening 64 of second body 60. The further first body 40 moves towards opening 22, the smaller the distance between first body 40 and second body 60. Second body 40 can moved in the direction of opening 22 for so long until the distance between first body 40 and second body 60 is closed, as shown in FIGS. 2A and 2B.

Figure 2B:
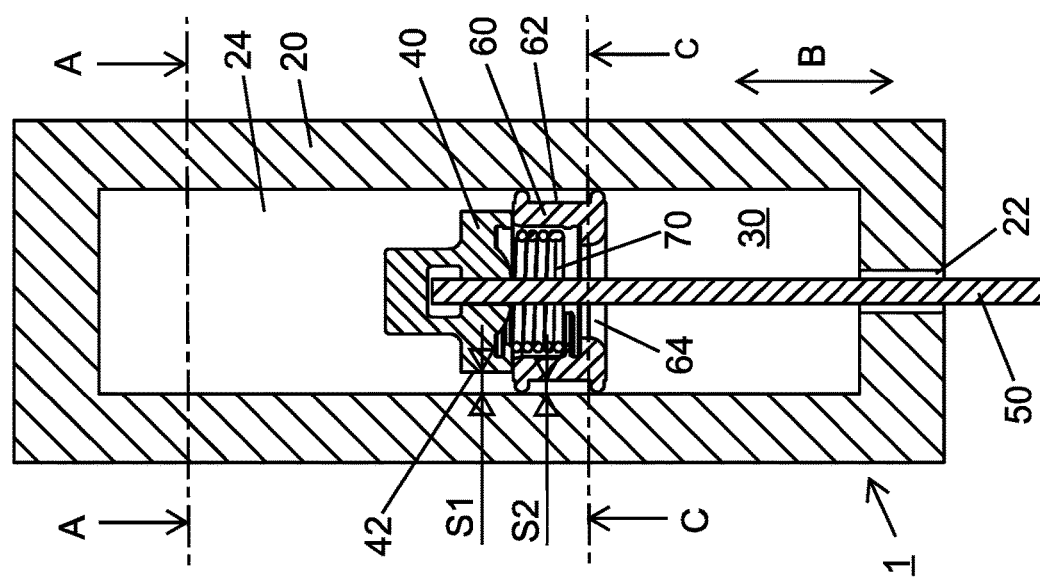
FIG. 2B shows a sectional view of the device from FIG. 1A in a holding state.
Figure 2A:
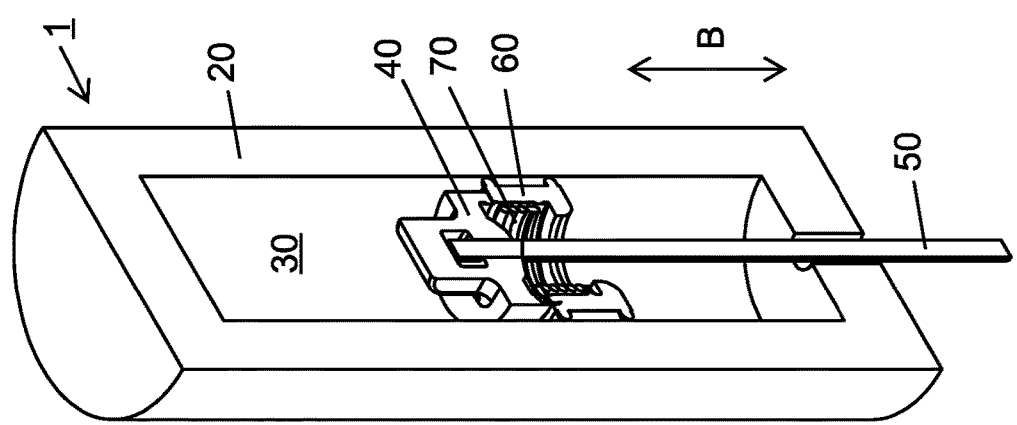
FIG. 2A shows a perspective sectional view of the device from FIG. 1A in a holding state.

In the state of device 1 shown in FIGS. 2A and 2B, first body 40 contacts second body 60 in such a manner that outlet opening 64 of second body 60 is closed. It is now only in the region between shear surfaces 42, 62 of first and of second body 40, 60 and of inner surface 26 that filling medium 30 located in inner space 24 has the possibility of flowing relative to first body 40 and second body 60 in so far as the degree of shear hardening allows.

In order to move first body 40 and second body 60 in the direction of opening 22, a holding force which results from the interaction of a sum of shear surface 42 and shear surface 62 with filling medium 30 must now be overcome. Device 1 is correspondingly able to provide a significantly larger holding force after closing outlet opening 64. In device 1 shown in FIGS. 1A, 1B, 1C, 2A and 2B, the speed-dependent resistance of device 1 against pulling out of force-transmission means 50 increases with the closing of outlet opening 64 by a factor of 50. Device 1 can correspondingly be dimensioned in such a manner that, in the case of an open outlet opening 64, a physiological force outlay of 20 N is necessary in order to move first body 40 relative to receptacle 20 and in the case of closed outlet opening 64 a force outlay of 1000 N is necessary in order to move first body 40 and second body 60 in the state lying next to one another relative to receptacle 20.

Figure 3A:
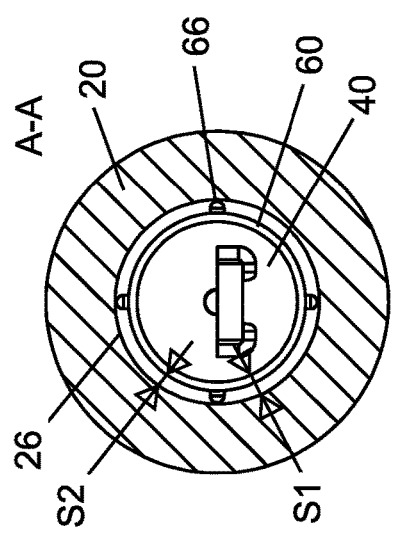
FIG. 3A shows a sectional view of the device from FIG. 1A along sectional line A-A from FIG. 2B.

FIG. 3A shows a sectional view along sectional line A-A from FIG. 2B. It can be inferred from FIG. 3A that guide projections 66 guide second body 60 along inner surface 26 of receptacle 20. Gap dimension S1 which represents the smallest distance between shear surface 42 and inner surface 26 and gap dimension S2 which represents the smallest distance between shear surface 62 and inner surface 26 can furthermore be inferred from FIG. 3A.

Figure 3B:
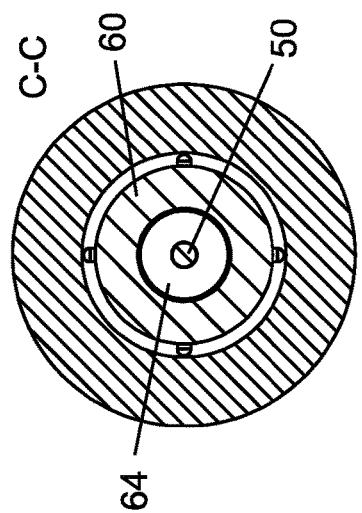
FIG. 3B shows a sectional view of the device from FIG. 1A along sectional line C-C from FIG. 2B.

FIG. 3B is a sectional view along sectional line C-C from FIG. 2B, from which outlet opening 64 in second body 60 can be inferred. FIG. 3B furthermore shows a concentric arrangement of force-transmission means 50 which extends through outlet opening 64 without touching second body 60.

Figure 4A:
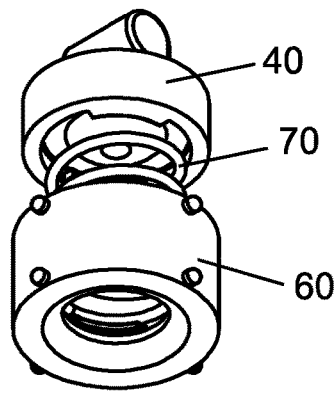
FIG. 4A shows a perspective view of the first body and of the second body in an initial state.

FIG. 4A shows a perspective view of first body 40, coupling element 70 and second body 60 in the state shown in FIG. 1.

Figure 4B:
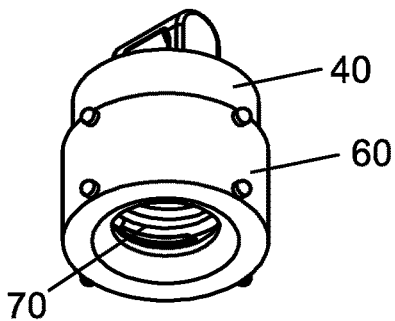
FIG. 4B shows a perspective view of the first body and of the second body in a compressed state.

FIG. 4B shows a perspective view of first body 40, coupling element 70 and second body 60 in the state shown in FIG. 2.

Figure 5:
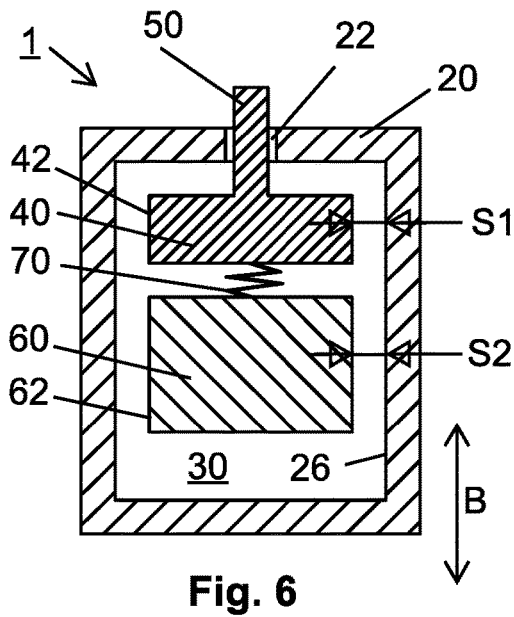
FIG. 5 shows a schematic sectional view of a device for stabilisation of joints, wherein the bodies have gap dimensions of different sizes.

FIG. 5 schematically shows a device 1 which is suitable for pressure loading. Force-transmission means 50 is connected to first body 40 in one piece and protrudes through opening 22 out of receptacle 20. If force-transmission means 50 is pushed into receptacle 20, first body 40 and second body 60 move away from opening 22. If the speed at which first body 40 moves away from opening 22 lies in the physiological range, second body 60 is pushed via coupling element 70 away from opening 22.

Second body 60 possesses a gap dimension S2 which is smaller than gap dimension S1 of first body 40. Moreover, shear surface 62 of second body 60 is larger than shear surface 42 of first body 40.

The ratio of the shear surfaces and the ratio of the gap dimensions of first body 40 and of second body 60 allows an increase in shear stress to occur in the region of shear surface 62 in the case of a speed in direction of movement B, in the case of which no or a significantly lower increase in shear stress occurs at shear surface 42. As a result, it is possible that second body 60 is blocked by the holding force, which is a result of the increase in shear stress, when a critical speed in direction of movement B is reached. In this situation, the holding force acting on second body 60 is greater than or equal to the opposite elastic force proceeding from coupling element 70.

If second body 60 is blocked as a result of the increase in shear stress in the region of shear surface 62 and if first body 40 is furthermore moved away from opening 22, the distance between first body 40 and second body 60 is reduced. In this state, the critical speed of first body 40 is defined by the size of shear surface 42 and gap dimension S1.

If the distance between first body 40 and second body 60 is closed by an ongoing force acting on force-transmission means 50, the critical speed at which an increase in shear stress occurs is defined by the sum of shear surfaces 42 and 62. A significantly larger holding force or resistance force acts counter to the compressive force acting on force-transmission means 50 after closing of the distance between first body 40 and second body 60.

Figure 6:
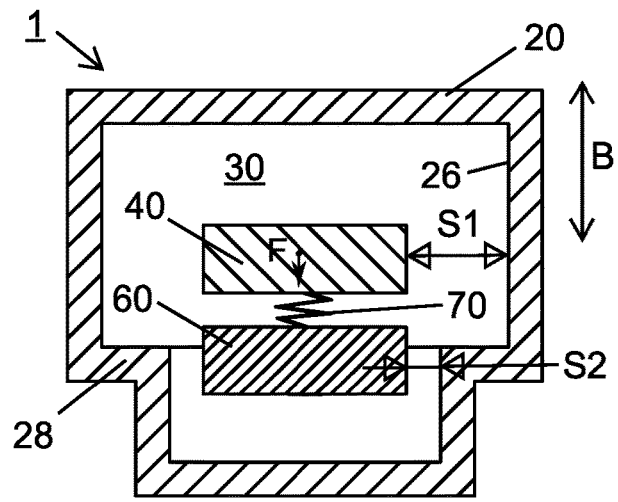
FIG. 6 shows a schematic sectional view of a device for stabilisation of joints, wherein the bodies have shear surfaces of different sizes.

Device 1 shown in FIG. 6 differs from the device shown in FIG. 5 in that gap dimension S1 between first body 40 and inner surface 26 is equal to gap dimension S2 between second body 60 and inner surface 26. Moreover, shear surface 62 of first body 40 is significantly larger than shear surface 42 of first body 40.

As a result, the speed in direction of movement B at which second body 60 is blocked as a result of the increase in shear stress of filling medium 30 in the region of shear surface 62 is lower than the speed in direction of movement B at which first body 40 is blocked as a result of the increase in shear stress of filling medium 30 in the region of shear surface 42.

Device 1 shown in FIG. 6 behaves like the device shown in FIG. 5 in the case of compressive loading of the force-transmission means into the interior of receptacle 20.

Figure 7:
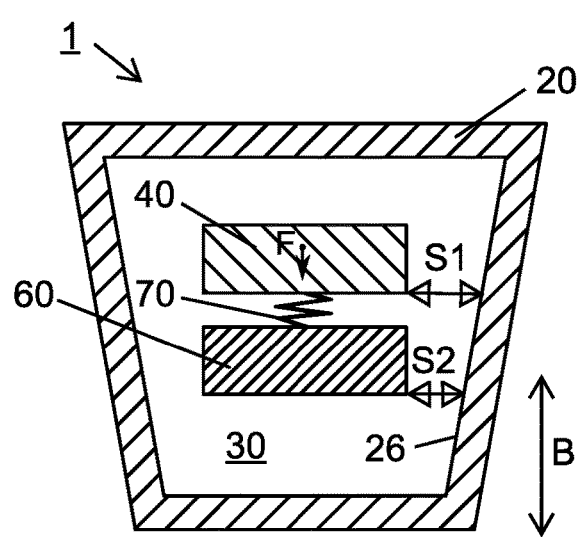
FIG. 7 shows a schematic sectional view of a device for stabilisation of joints, wherein the receptacle has a step.

FIG. 7 shows a simplified representation of receptacle 20 and first body 40 arranged therein which is connected via coupling element 70 to second body 60. The profile of receptacle 20 has a step 28 by which receptacle 20 in a region with a large diameter and a region with a small diameter is defined. For the sake of simplicity, the force-transmission means is not represented in FIG. 7. However, FIG. 7 shows an arrow which represents an external force F which points in the direction of the region of the receptacle with a smaller diameter. First body 40 and second body 60 have the same dimensions. Alternatively, the dimensions can also vary as shown in FIGS. 5 and 6. First body 40 and second body 60 are arranged in such a manner that, in the case of a movement in direction of movement B towards the region of receptacle 20 with the smaller diameter, second body 60 reaches this region before first body 40.

If first body 40 and second body 60 move through the region of receptacle 20 with the larger diameter, both bodies are spaced apart by gap dimension S1 from inner surface 26 of receptacle 20. If second body 60 reaches the region of receptacle 20 with the smaller diameter, second body 60 is now only spaced apart by gap dimension S2 from inner surface 26 of receptacle 20. As is apparent from FIG. 7, gap dimension S2 is smaller than gap dimension S1. By reaching the region of receptacle 20 with the smaller diameter, as represented in FIG. 7, the speed reduces at which second body 60 is blocked as a result of the shear hardening of filling medium 30 and cannot move further. The further behaviour of the device corresponds to that of the devices from FIGS. 5 and 6.

Figure 8:
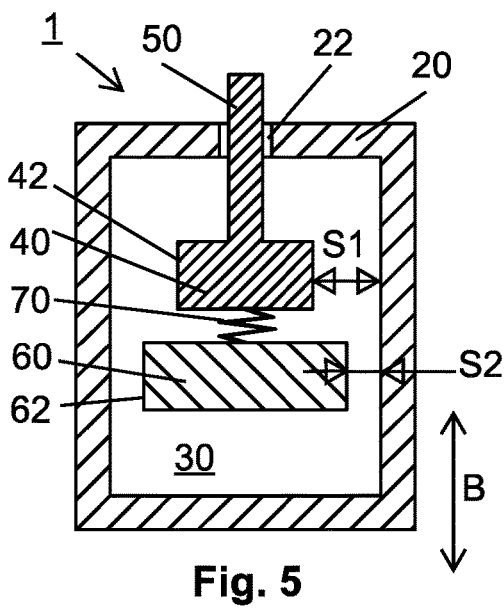
FIG. 8 shows a schematic sectional view of a device for stabilisation of joints, wherein the receptacle has a conical form.

FIG. 8 shows a simplified representation of a device 1 which differs from the device shown in FIG. 7 in that the surface of receptacle 20 runs conically in direction of movement B. As a result of the conical configuration of receptacle 20, in the case of the same dimension of first body 40 and of second body 60, gap dimension S1 of first body 40 is always larger than gap dimension S2 of second body 60. The behaviour of device 1 shown in FIG. 8 as a result of the introduction of a force F onto the first body corresponds to the behaviour of the devices from FIGS. 5, 6 and 7.

In order to return the devices represented in the above figures to an initial position, restoring means can be provided. These restoring means can be embodied, for example, elastically and connect the first body to the opposite side in the direction of movement of the receptacle. If the first body is deflected out of the initial position by an acting force, the elastic restoring means is expanded. If the external force and the holding force of the shear hardening abate, the elastic restoring means can convey the first body, the coupling element and the second body back into the initial position as a result of the previously experienced expansion.

The device can be used, for example, in the following products: shoes, trousers, jackets, shirts, stockings, gloves, protectors, protective clothing, prostheses, bandages, orthotics, tapes, helmets, shin guards, boots, dressings, etc.

Where applicable, all of the individual features which are represented in the individual exemplary embodiments can be combined with one another and/or exchanged without departing from the scope of the invention.

LIST OF REFERENCE SIGNS

1 Device
20 Receptacle
22 Opening
24 Inner space
26 Inner surface
28 Step
30 Filling medium
40 First body
42 Shear surface
44 Force-transmission region
46 Spring seat
50 Force-transmission means
60 Second body
62 Shear surface
64 Outlet opening
66 Guide projection
68 Spring seat
70 Coupling element
S1 Gap dimension
S2 Gap dimension
B Direction of movement
F Force

The invention claimed is:

1. A device for stabilizing joints, comprising:
a receptacle of the device for stabilizing joints, wherein the receptacle is filled with a filling medium,
a first body for interaction with the filling medium, wherein the first body is arranged displaceably in the receptacle,
a force transmitter configured to directly transmit an external force onto the first body,
a second body for interaction with the filling medium, wherein the second body is arranged displaceably in the receptacle,
wherein the second body is coupled elastically to the first body via a coupling element disposed between the first body and the second body,
wherein at least one of the second body and the first body have at least one outlet opening through which the filling medium can flow,
wherein the first body forms a valve body of a valve and the second body forms a valve seat of the valve, and the first body and the second body are configured to open to allow or close to prevent a flow of the filling medium between one side of the receptacle and another side of the receptacle through the at least one outlet based on an open or closed position of the valve, wherein the second body divides the receptacle into the one side of the receptacle and another side of the receptacle, and
wherein the valve is configured such that the position of the valve is open when the first body is out of contact with the second body and is closed when the first body moves towards and contacts the second body.

2. The device of claim 1, further comprising:
the first body having a shear surface and the second body having a shear surface of a different size than the shear surface of the first body.

3. The device of claim 2, wherein the shear surface of the first body is smaller than the shear surface of the second body.

4. The device of claim 1, further comprising:
a gap dimension between the first body and the receptacle, and
a gap dimension between the second body and the receptacle that is different from the gap dimension between the first body and the receptacle.

5. The device of claim 4, wherein the gap dimension between the first body and the receptacle is larger than the gap dimension between the second body and the receptacle.

6. The device of claim 1, wherein the coupling element comprises at least one spring element.

7. The device of claim 1, wherein the coupling element comprises a material with a temperature-dependent modulus of elasticity.

8. The device of claim 1, wherein the at least one outlet opening is configured to be closed by at least one of the first body, the second body, or both, to prevent a flow of the filling medium through the outlet opening.

9. The device of claim 1, wherein the force transmitter for transmission of the external force is formed in one piece with the first body.

10. The device of to claim 1, wherein the first body is configured to exert a compressive force and/or a tractive force on the second body by means of the coupling element.

11. The device of claim 1, further comprising:
a size of a shear surface of the first body; and
a size of a shear surface of the second body;
wherein the size of the shear surface of the first body and the size of the shear surface of the second body are configured to, if an external force acts with a speed below a threshold value on the first body, move the first body and the second body substantially uniformly through the filling medium, and
if the external force acts with a speed greater than or equal to the threshold value on the first body, move the first body and the second body relative to one another.

12. The device of claim 1, wherein the filling medium is a fluid.

13. The device of claim 1, wherein the filling medium is a shear-thickening filling medium.

* * * * *